United States Patent [19]

Midorikawa et al.

[11] Patent Number: 5,663,113
[45] Date of Patent: Sep. 2, 1997

[54] AMMOXIDATION CATALYST COMPOSITION

[75] Inventors: Hideo Midorikawa; Ken Someya, both of Kurashiki, Japan

[73] Assignee: Asahi Kasei Kogyo Kabushiki Kaisha, Osaka, Japan

[21] Appl. No.: 603,003

[22] Filed: Feb. 16, 1996

[51] Int. Cl.$^6$ ....................................... B01J 23/00
[52] U.S. Cl. .................... 502/314; 502/311; 502/316; 502/321; 558/319; 558/323; 558/324
[58] Field of Search .................. 502/321, 324, 502/311, 313, 314, 316; 558/319–324

[56] References Cited

U.S. PATENT DOCUMENTS

| | | |
|---|---|---|
| 3,226,422 | 12/1965 | Sennewald et al. . |
| 3,969,390 | 7/1976 | Faletti et al. . |
| 4,192,776 | 3/1980 | Grasselli et al. . |
| 4,377,534 | 3/1983 | Grasselli et al. .......................... 502/321 |
| 4,443,556 | 4/1984 | Aoki et al. . |
| 4,495,109 | 1/1985 | Grasselli et al. .......................... 502/321 |
| 4,503,001 | 3/1985 | Grasselli et al. .......................... 502/321 |
| 4,746,753 | 5/1988 | Brazdil et al. . |
| 4,767,739 | 8/1988 | Glaeser et al. ............................ 502/209 |
| 4,921,828 | 5/1990 | Brazdil et al. . |
| 4,939,286 | 7/1990 | Brazdil et al. . |
| 4,978,764 | 12/1990 | Seely et al. ............................... 558/319 |
| 5,093,299 | 3/1992 | Suresh et al. . |
| 5,175,334 | 12/1992 | Suresh et al. . |
| 5,212,137 | 5/1993 | Suresh et al. . |
| 5,470,815 | 11/1995 | Kim et al. ................................ 502/321 |

FOREIGN PATENT DOCUMENTS

| | | |
|---|---|---|
| 38-17967 | of 1960 | Japan . |
| 38-19111 | of 1960 | Japan . |
| 49-101331 | of 1974 | Japan . |
| 51-33888 | of 1976 | Japan . |
| 57-180431 | of 1982 | Japan . |
| 58-38424 | of 1983 | Japan . |
| 59-204163 | of 1984 | Japan . |
| 61-43094 | of 1986 | Japan . |
| 61-26419 | of 1986 | Japan . |
| 5-13707 | of 1993 | Japan . |
| 1445512 | 8/1976 | United Kingdom . |

*Primary Examiner*—Steven Bos
*Assistant Examiner*—Thomas G. Dunn, Jr.
*Attorney, Agent, or Firm*—Pennie & Edmonds LLP

[57] ABSTRACT

Disclosed is an ammoxidation catalyst composition for use in producing acrylonitrile from propylene, or methacrylonitrile from isobutene or tert-butanol, by ammoxidation of the propylene or of the isobutene or tert-butanol, comprising an oxide catalyst composition represented by the formula:

$$Mo_{12}(Bi_{1-a}A_a)_b Fe_c Co_d X_e Y_f O_g,$$

wherein A is at least one rare earth element, X is at least one element selected from the group consisting of nickel, magnesium, zinc and manganese, Y is at least one element selected from the group consisting of potassium, rubidium and cesium, a is a number of from 0.6 to 0.8, b is a number of from 0.5 to 2, c is a number of from 0.1 to 3, d is a number of from more than 0 to 10, e is a number of from 0 to 8, f is a number of from 0.01 to 2, and g is a number determined by the valence requirements of the other elements present. By use of the ammoxidation catalyst composition of the present invention, not only can acrylonitrile and methacrylonitrile be produced in high yield, but also the ammoxidation reaction can be stably conducted even when the operation of the production process is conducted for a prolonged period of time, so that a lowering of the yield of acrylonitrile or methacrylonitrile is very small.

15 Claims, No Drawings

AMMOXIDATION CATALYST COMPOSITION

BACKGROUND OF THE INVENTION

1. Technical Field

The present invention relates to an ammoxidation catalyst composition, and a process for producing acrylonitrile or methacrylonitrile using the same. More particularly, the present invention is concerned with an ammoxidation catalyst composition for use in the process for producing acrylonitrile or methacrylonitrile by reacting propylene with, or reacting isobutene or tert-butanol with molecular oxygen and ammonia, the ammoxidation catalyst composition comprising an oxide catalyst composition comprised of molybdenum, bismuth, at least one rare earth element, iron, cobalt, at least one element selected from the group consisting of nickel, magnesium, zinc and manganese, and at least one element selected from the group consisting of potassium, rubidium and cesium, wherein the atomic ratio of the sum of bismuth and the at least one rare earth element, relative to twelve atoms of molybdenum, is from 0.5 to 2 and the atomic ratio of the at least one rare earth element to the sum of bismuth and the at least one rare earth element is from 0.6 to 0.8. By use of such an ammoxidation catalyst composition, not only can acrylonitrile or methacrylonitrile be produced in high yield, but also a lowering of the yield of acrylonitrile or methacrylonitrile can be effectively suppressed even after the operation of the production process has been conducted for a prolonged period of time. The present invention is also concerned with a process for producing acrylonitrile or methacrylonitrile using such an ammoxidation catalyst composition.

2. Prior Art

It has been well known to produce acrylonitrile or methacrylonitrile by ammoxidation of propylene, or of isobutene or tert-butanol, namely, a reaction of propylene with, or of isobutene or tert-butanol with molecular oxygen and ammonia. A number of proposals have been made with respect to catalysts for use in the ammoxidation of propylene, or of isobutene or tert-butanol. For example, Examined Japanese Patent Application Publication No. 38-17967 proposes an oxide catalyst containing molybdenum, bismuth and iron, and Examined Japanese Patent Application Publication No. 38-19111 proposes an oxide catalyst containing antimony and iron. Further, various improvements have been proposed with respect to these ammoxidation catalyst systems.

For example, each of Unexamined Japanese Patent Application Laid-Open Specification No. 49-101331 (corresponding to British Patent No. 1,445,512) and Unexamined Japanese Patent Application Laid-Open Specification No. 57-180431 (corresponding to U.S. Pat. No. 4,746,753) discloses a catalyst containing an alkali metal and thallium in addition to molybdenum, bismuth and cerium. Examined Japanese Patent Application Publication No. 61-43094 discloses a catalyst comprising molybdenum, tungsten, bismuth and cerium. Examined Japanese Patent Application Publication 58-38424 (corresponding to U.S. Pat. No. 3,969,390) discloses an oxide catalyst containing at least one element selected from iron, chromium, aluminum and bismuth, in addition to molybdenum, tellurium and cerium. Examined Japanese Patent Application Publication No. 51-33888 (corresponding to U.S. Pat. No. 4,192,776) discloses an oxide catalyst containing, in addition to molybdenum, bismuth and iron, at least one element selected from nickel and cobalt, and at least one element selected from an alkali metal, a rare earth element, tantalum and niobium. Examined Japanese Patent Application Publication No. 61-26419 (corresponding to U.S. Pat. No. 4,443,556) discloses an oxide catalyst containing molybdenum, bismuth and iron as essential elements, and also containing at least one element selected from cerium, lanthanum, neodymium, praseodymium, samarium, europium and gadolinium, and at least one element selected from potassium, rubidium and cesium. Unexamined Japanese Patent Application Laid-Open Specification No. 59-204163 discloses a catalyst containing, in addition to molybdenum, bismuth, phosphorus and silicon, at least two elements selected from iron, cobalt, nickel, copper, zirconium and potassium, and at least one element selected from manganese, cerium, thorium, yttrium, lanthanum and thallium. However, in the above prior art documents, there are no working examples using a catalyst composition satisfying the specific requirements of the catalyst composition of the present invention.

Further, each of U.S. Pat. No. 5,093,299, U.S. Pat. No. 5,175,334 and U.S. Pat. No. 5,212,137 discloses a catalyst containing molybdenum, bismuth, iron, nickel, magnesium, potassium and cesium as essential elements and optionally containing cobalt, manganese, chromium, phosphorus, antimony, tellurium, sodium, cerium and/or tungsten, and a process for producing acrylonitrile or methacrylonitrile using such a catalyst. However, it is noted that in the working examples of the above three U.S. patent documents, a catalyst containing cerium is not used. It is needless to say that, in these patent documents, neither working example nor description is found with respect to use of any other rare earth element.

The catalysts disclosed in the above-mentioned patent documents are greatly improved in respect of the yield of acrylonitrile or methacrylonitrile at the initial stage of reaction. However, those catalysts are still unsatisfactory in respect of the yield of acrylonitrile or methacrylonitrile when the operation Of the production process is conducted for a prolonged period of time.

DISCLOSURE OF THE INVENTION

In the above situations, the present inventors have made extensive and intensive studies toward developing a catalyst for use in ammoxidation, which is free from the above-mentioned problem, and which can be advantageously used not only for producing acrylonitrile or methacrylonitrile in high yield, but also for performing a stable ammoxidation reaction even when the operation of the production process is conducted for a prolonged period of time, so that a lowering of the yield of acrylonitrile or methacrylonitrile is small. As a result, it has been found that when an oxide catalyst composition, which is represented by the formula (I):

$$Mo_{12}(Bi_{1-a}A_a)_b Fe_c Co_d X_e Y_f O_g \qquad (I)$$

wherein:

A is at least one rare earth element,

X is at least one element selected from the group consisting of nickel, magnesium, zinc and manganese, Y is at least one element selected from the group consisting of potassium, rubidium and cesium, a is the atomic ratio of A to the sum of bismuth and A, b is the atomic ratio of the sum of bismuth and A, relative to twelve atoms of molybdenum, and c, d, e, f and g are, respectively, the atomic ratios of iron, cobalt, X, Y and oxygen, relative to twelve atoms of molybdenum, wherein
  a is a number of from 0.6 to 0.8,
  b is a number of from 0.5 to 2,
  c is a number of from 0.1 to 3,
  d is a number of from more than 0 to 10,
  e is a number of from 0 to 8,
  f is a number of from 0.01 to 2, and
  g is a number determined by the valence requirements of the other elements present, is used as an ammoxidation catalyst in the process for producing acrylonitrile or methacrylonitrile by reacting propylene with, or reacting isobutene or tert-butanol with molecular oxygen and ammonia, not only can acrylonitrile or methacrylonitrile be produced in high yield, but also the ammoxidation reaction can be stably conducted even when the operation of the production process is conducted for a prolonged period of time, so that a lowering of the yield of acrylonitrile or methacrylonitrile is very small. The present invention has been made based on this novel finding.

Accordingly, it is an object of the present invention to provide an ammoxidation catalyst composition, by use of which not only can acrylonitrile or methacrylonitrile be produced in high yield, but also the ammoxidation reaction can be stably conducted even when the operation of the production process is conducted for a prolonged period of time, so that a lowering of the yield of acrylonitrile or methacrylonitrile is very small.

It is another object of the present invention to provide a process for producing acrylonitrile or methacrylonitrile using the above-mentioned novel ammoxidation catalyst composition.

The foregoing and other objects, features and advantages of the present invention will be apparent from the following detailed description and appended claims.

DETAILED DESCRIPTION OF THE INVENTION

In one aspect of the present invention, there is provided an ammoxidation catalyst composition comprising an oxide catalyst composition represented by the formula (I):

$$Mo_{12}(Bi_{1-a}A_a)_b Fe_c Co_d X_e Y_f O_g \qquad (I)$$

wherein:
  A is at least one rare earth element,
  X is at least one element selected from the group consisting of nickel, magnesium, zinc and manganese,
  Y is at least one element selected from the group consisting of potassium, rubidium and cesium,
  a is the atomic ratio of A to the sum of bismuth and A,
  b is the atomic ratio of the sum of bismuth and A, relative to twelve atoms of molybdenum, and
  c, d, e, f and g are, respectively, the atomic ratios of iron, cobalt, X, Y and oxygen, relative to twelve atoms of molybdenum,
wherein
  a is a number of from 0.6 to 0.8,
  b is a number of from 0.5 to 2,
  c is a number of from 0.1 to 3,
  d is a number of from more than 0 to 10,
  e is a number of from 0 to 8,
  f is a number of from 0.01 to 2, and
  g is a number determined by the valence requirements of the other elements present.

The ammoxidation catalyst composition of the present invention has a characteristic feature in that the atomic ratio b of the sum of bismuth and A, relative to twelve atoms of molybdenum, is from 0.5 to 2, preferably 0.7 to 1.8, and the atomic ratio a of A to the sum of bismuth and A is from 0.6 to 0.8. When b is less than 0.5 or is more than 2, not only does the yield of acrylonitrile or methacrylonitrile at the initial stage of reaction become low, but also the ammoxidation reaction becomes unstable. When a is less than 0.6, although the yield of acrylonitrile or methacrylonitrile is good at the initial stage of reaction, not only is the ammoxidation reaction unstable but the yield of acrylonitrile or methacrylonitrile is also drastically lowered with the lapse of operation time. On the other hand, when a is more than 0.8, the yield of acrylonitrile or methacrylonitrile is disadvantageously lowered even at the initial stage of reaction. A is at least one rare earth element. By the term "at least one rare earth element" are meant one or more elements selected from the group consisting of scandium, yttrium, lanthanum, cerium, praseodymium, neodymium, promethium, samarium, europium, gadolinium, terbium, dysprosium, holmium, erbium, thulium, ytterbium and lutetium, which are classified as rare earth elements in the Periodic Table. Of the above-mentioned rare earth elements, yttrium, lanthanum, cerium, praseodymium, neodymium and samarium are preferred. Cerium is more preferred. With respect to c, d, e and f, which are, respectively, the atomic ratios of iron, cobalt, X (which is at least one element selected from nickel, magnesium, zinc and manganese) and Y (which is at least one element selected from potassium, rubidium and cesium), relative to twelve atoms of molybdenum, c is from 0.1 to 3, preferably from 0.5 to 2.5; d is from more than 0 to 10, preferably from 0.5 to 8; e is from 0 to 8, preferably from 0.1 to 6; and f is from 0.01 to 2, preferably from 0.02 to 1. A catalyst composition in which c, d, e and f are in the above-mentioned range has high catalyst activity and high selectivity, so that the yield of acrylonitrile or methacrylonitrile is high.

With respect to a carrier which can be used to support thereon the oxide catalyst composition of the present invention, oxides, such as silica, alumina, titania and zirconia, can be employed. Of these oxides, silica is preferred. Silica is inherently inert, differing from other carrier materials, and can serve as an excellent binder for the ingredients of the oxide catalyst composition without impairing the selectivity of the oxide catalyst composition and serve to impart the resulting catalyst composition with a high attrition resistance. The amount of carrier to be used may be in the range of from 30 to 70% by weight, preferably from 40 to 60% by weight, based on the total weight of the oxide catalyst composition and the carrier. When the amount of carrier to be used is less than 30% by weight, physical strength of the resultant catalyst composition is not sufficient. When the amount of the carrier to be used is more than 70% by weight, the yield of acrylonitrile or methacrylonitrile becomes low.

The ammoxidation catalyst composition of the present invention can be produced by a conventional method. For example, the ammoxidation catalyst composition can be produced by a method comprising the steps of (1) preparing a slurry of starting materials, (2) spray-drying the slurry prepared in step (1) above to obtain a dried particulate catalyst precursor, and (3) subjecting the dried particulate catalyst precursor obtained in step (2) above to calcination and firing, successively.

Hereinbelow, explanation is made with respect to a preferred mode of the above-mentioned method for producing the ammoxidation catalyst composition of the present invention, which comprises steps (1), (2) and (3), above.

In step (1), a slurry of starting materials prepared. In the starting materials, each of the elements (which are to be incorporated into a catalyst composition), i.e., molybdenum, bismuth, at least one rare earth element, iron, cobalt, nickel, magnesium, zinc, manganese, potassium, rubidium and cesium, may be present in the form of an ammonium salt, a nitrate, a chloride, a sulfate and/or an organic acid salt, which are soluble in water or nitric acid. Especially, it is preferred that a molybdenum source be in the form of an ammonium salt, and that each of bismuth, at least one rare earth element, iron, cobalt, nickel, magnesium, zinc, manganese, potassium, rubidium and cesium be used in the form of a nitrate.

As mentioned above, in the ammoxidation catalyst composition of the present invention, an oxide, such as silica, alumina, titania or zirconia, can be employed as a carrier for the oxide catalyst composition represented by formula (I). Of the above oxides, silica is most advantageously used. As the source of silica, a silica sol is preferred.

The slurry of starting materials can be prepared by, for example, adding a solution of nitrates of component metals except molybdenum (i.e., sources of bismuth, at least one rare earth element, iron, cobalt, nickel, magnesium, zinc, manganese, potassium, rubidium and cesium) in water or in aqueous nitric acid to a silica sol, followed by addition of an aqueous ammonium molybdate solution. Alternatively, for preparing the slurry of starting materials, the above-mentioned aqueous ammonium molybdate solution may be first added to a silica sol, followed by addition of the above-mentioned solution of nitrates of component metals except molybdenum.

In step (2), the slurry obtained in step (1) above is subjected to spray drying, to thereby obtain a quasi-spherical particulate catalyst precursor. The spray drying of the slurry can be generally conducted by centrifugation, two-phase flow nozzle method or high pressure nozzle method to obtain a dried particulate catalyst precursor.

In this instance, it is preferred to use air which has been heated by an electric heater, steam or the like, as a heat source for drying. In this case, it is preferred that the temperature of the spray dryer at an entrance thereof be from 100° to 400° C., preferably 150° to 300° C.

In step (3), the dried particulate catalyst precursor obtained in step (2) above is calcined and finally fired to thereby obtain a desired oxide catalyst composition. The dried particulate catalyst is calcined at a temperature of from 150° to 500° C., and then subjected to firing at a temperature of from 500° to 750° C., preferably from 550° to 700° C. for 1 to 20 hours. For the calcination and firing, a kiln, such as a rotary kiln, a tunnel kiln or a muffle kiln, can be used.

When the ammoxidation catalyst composition of the present invention comprises an oxide catalyst composition supported on a carrier (preferably silica), it is preferred that the particle diameter distribution of the ammoxidation catalyst composition be within the range of from 10 to 150 μm.

The process for producing acrylonitrile or methacrylonitrile by reacting propylene with, or reacting isobutene or tert-butanol with molecular oxygen and ammonia in the presence of an ammoxidation catalyst composition of the present invention may be conducted either in a fluidized bed reactor or in a fixed bed reactor. However, a fluidized bed reactor is preferred.

Propylene, isobutene or tert-butanol and ammonia to be used in the process of the present invention need not necessarily be of very high purity but may be of a commercial grade. As a source of oxygen, air is usually employed. Gas having an increased oxygen content such as a gaseous mixture of air and oxygen, is also usable.

In the process of the present invention, it is advantageous that the molar ratios of propylene, or isobutene or tert-butanol:ammonia:air be in the range of 1:08 to 1.4:7 to 12, preferably 1:0.9 to 1.3:8 to 11. It is advantageous that the molar ratios of propylene, or isobutene or tert-butanol:ammonia:oxygen be in the range of 1:0.8 to 1.4:1.4 to 2.4, preferably 1:0.9 to 1.3:1.6 to 2.2. The reaction temperature may be from 350° to 550° C., preferably from 400° to 500° C. The reaction may usually be conducted under a pressure of from atmospheric pressure to 3 atm. The time of contact between a gaseous mixture of raw materials and the catalyst composition (contact time) may be from 0.5 to 20 sec·g/cc, preferably from 1 to 10 sec·g/cc.

Thus, in another aspect of the present invention, there is provided a process for producing acrylonitrile from propylene, or methacrylonitrile from isobutene or tert-butanol, by ammoxidation of the propylene or of the isobutene or tert-butanol, which comprises reacting propylene with, or reacting isobutene or tert-butanol with molecular oxygen and ammonia at a temperature of from 350° C. to 550° C. under a pressure of from atmospheric pressure to 3 atm in the presence of an ammoxidation catalyst composition comprising an oxide catalyst composition represented by the formula (I):

$$Mo_{12}(Bi_{1-a}A_a)_b Fe_c Co_d X_e Y_f O_g \qquad (I)$$

wherein:

A is at least one rare earth element,

X is at least one element selected from the group consisting of nickel, magnesium, zinc and manganese, Y is at least one element selected from the group consisting of potassium, rubidium and cesium, a is the atomic ratio of A to the sum of bismuth and A, b is the atomic ratio of the sum of bismuth and A, relative to twelve atoms of molybdenum, and c, d, e, f and g are, respectively, the atomic ratios of iron, cobalt, X, Y and oxygen, relative to twelve atoms of molybdenum, wherein
  a is a number of from 0.6 to 0.8,
  b is a number of from 0.5 to 2,
  c is a number of from 0.1 to 3,
  d is a number of from more than 0 to 10,
  e is a number of from 0 to 8,
  f is a number of from 0.01 to 2, and
  g is determined by the valence requirements of the other elements present.

As mentioned above, by use of the ammoxidation catalyst composition of the present invention in the process for producing acrylonitrile or methacrylonitrile by reacting propylene with, or reacting isobutene or tert-butanol with molecular oxygen and ammonia, not only can acrylonitrile or methacrylonitrile be produced in high yield, but also the ammoxidation reaction can be stably conducted for a prolonged period of time, so that a lowering of the yield of acrylonitrile or methacrylonitrile is very small.

BEST MODE FOR CARRYING OUT THE INVENTION

Hereinbelow, the present invention will be described in more detail with reference to the following Examples and Comparative Examples, but they should not be construed as limiting the scope of the present invention.

In the following Examples and Comparative Examples, the conversion and yield used for evaluating the results of the reaction are defined as follows:

$$\text{Conversion (\%)} = \frac{\text{mole of propylene, isobutene or tert-butanol reacted}}{\text{mole of propylene, isobutene or tert-butanol fed}} \times 100$$

$$\text{Yield (\%)} = \frac{\text{mole of acrylonitrile or methacrylonitrile formed}}{\text{mole of propylene, isobutene or tert-butanol fed}} \times 100$$

A stainless steel (SUS 304) fluidized bed reactor having an outer diameter of 3 inches was used as a reaction apparatus. The reaction pressure (P) was maintained at 0.5 kg/cm$^2$·G, and the reaction temperature (T) was maintained at 440° C. The amount (W) of a catalyst charged in the reactor was 1,000 to 2,000 g, and the total flow rate (F) of raw material gases introduced into the reactor was 100 to 150 cc/sec in terms of the volume per unit time under normal temperature and pressure (N.T.P) conditions.

The contact time is defined by the following formula:

$$\text{Contact time (sec·g/cc)} = (W/F) \times 273/(273+T) \times (1.03+P)/1.03.$$

The compositions of raw material gases introduced into the reactor were as follows:

for an ammoxidation reaction of propylene:

*propylene/ammonia/air*=1/1.1/8.0–10.0.

for an ammoxidation reaction of isobutene or tert-butanol:

*isobutene or tert-butanol/ammonia/air*=1/1.2/9.0–10.5.

EXAMPLE 1

An ammoxidation catalyst composition, composed of oxides supported on 50% by weight, based on the total weight of the oxides and silica, of silica, having a structure represented by the formula:

$$Mo_{12}Bi_{0.20}Ce_{0.40}Fe_{2.0}Co_{7.8}K_{0.07}Cs_{0.04},$$

was prepared as follows.

37.6 g of bismuth nitrate [Bi(NO$_3$)$_3$·5H$_2$O], 68.4 g of cerium nitrate [Ce(NO$_3$)$_3$·6H$_2$O], 314.8 g of iron nitrate [Fe(NO$_3$)$_3$·9H$_2$O], 884.6 g of cobalt nitrate [Co(NO$_3$)$_2$·6H$_2$O], 2.74 g of potassium nitrate [KNO$_3$] and 3.04 g of cesium nitrate [CsNO$_3$] were dissolved in 746.5 g of a 17.9 wt % aqueous nitric acid solution. The resultant solution was added to 3,333.4 g of a silica sol having a SiO$_2$ content of 30 wt %, to obtain a mixture. To the thus obtained mixture was added a solution of 822.9 g of ammonium paramolybdate [(NH$_4$)$_6$Mo$_7$O$_{24}$·4H$_2$O] in 1,645.9 g of water, to thereby obtain a slurry The slurry thus obtained was fed to a parallel flow type spray-drying apparatus, in which the slurry was atomized by means of a sprayer having a dish type rotor disposed above the central portion of a dryer of the spray-drying apparatus, and dried at about 200° C., to thereby obtain a dried particulate catalyst precursor. The obtained dried particulate catalyst precursor was calcined in an electric kiln at 400° C. for 1 hour and then subjected to firing at 580° C. for 2 hours, thereby obtaining a catalyst composition supported on the silica.

Using 1,400 g of the obtained catalyst composition supported on the silica, an ammoxidation reaction of propylene was conducted. The contact time in the ammoxidation was 6.5 sec·g/cc. Results of the reaction were evaluated at time points of 100 hours, 700 hours and 1,400 hours after the start of reaction. As a result, it was found that 100 hours after the start of reaction, the conversion of propylene was 99.6%, and the yield of acrylonitrile was 80.7%; that 700 hours after the start of reaction, the conversion of propylene was 99.4%, and the yield of acrylonitrile was 80.2%; and that 1,400 hours after the start of reaction, the conversion of propylene was 99.2%, and the yield of acrylonitrile was 79.8%.

EXAMPLES 2 TO 15 AND COMPARATIVE EXAMPLES 1 TO 5

Ammoxidation catalyst compositions, composed of oxides supported on 50% by weight, based on the total weight of the oxides and silica, of silica, having the respective compositions indicated in Table 1 were prepared in substantially the same manner as in Example 1. Using the obtained catalyst compositions individually, ammoxidation reactions of propylene were conducted. Results are shown in Table 1.

TABLE 1

| | Mo | Bi | A | Fe | Co | X | Y | | a | b |
|---|---|---|---|---|---|---|---|---|---|---|
| Example 1 | 12 | 0.20 | Ce 0.40 | 2.0 | 7.8 | — | K 0.09 | Cs 0.04 | 0.67 | 0.60 |
| Example 2 | 12 | 0.45 | Ce 0.90 | 1.8 | 7.0 | — | | Rb 0.14 | 0.67 | 1.35 |
| Example 3 | 12 | 0.45 | Ce 0.90 | 1.8 | 5.0 | Mg 2.0 | K 0.09 | Rb 0.05 | 0.67 | 1.35 |
| Example 4 | 12 | 0.60 | Ce 1.20 | 1.8 | 4.5 | Mg 2.0 | K 0.20 | | 0.67 | 1.80 |
| Example 5 | 12 | 0.27 | Ce 1.08 | 1.8 | 6.5 | Mn 0.5 | K 0.11 | Cs 0.03 | 0.80 | 1.35 |
| Example 6 | 12 | 0.54 | Ce 0.81 | 1.8 | 5.0 | Zn 2.0 | Cs 0.10 | | 0.60 | 1.35 |
| Example 7 | 12 | 0.39 | Ce 0.96 | 1.8 | 6.0 | Ni 1.0 | K 0.09 | Rb 0.05 | 0.71 | 1.35 |
| Example 8 | 12 | 0.39 | Ce 0.96 | 1.8 | 1.0 | Ni 6.0 | K 0.09 | Rb 0.05 | 0.71 | 1.35 |
| Example 9 | 12 | 0.39 | Ce 0.96 | 1.8 | 3.5 | Ni 3.5 | K 0.09 | Rb 0.05 | 0.71 | 1.35 |
| Example 10 | 12 | 0.39 | Ce 0.96 | 1.8 | 3.0 | Ni 2.0 Mg 2.0 | K 0.09 | Rb 0.05 | 0.71 | 1.35 |
| Example 11 | 12 | 0.30 | Y 0.60 | 2.0 | 3.0 | Ni 4.5 | K 0.07 | Rb 0.04 | 0.67 | 0.90 |

TABLE 1-continued

| | | | | | | | | | | | | |
|---|---|---|---|---|---|---|---|---|---|---|---|---|
| Example 12 | 12 | 0.30 | La 0.60 | | | 2.0 | 3.0 Ni 4.5 | | | K 0.07 | Rb 0.04 | 0.67 | 0.90 |
| Example 13 | 12 | 0.30 | Pr 0.13 | Nd | 0.47 | 2.0 | 3.0 Ni 4.5 | | | K 0.07 | Rb 0.04 | 0.67 | 0.90 |
| Example 14 | 12 | 0.30 | Sm 0.60 | | | 2.0 | 3.0 Ni 4.5 | | | K 0.07 | Rb 0.04 | 0.67 | 0.90 |
| Example 15 | 12 | 0.45 | Ce 0.90 | | | 1.9 | 7.3 — | | | K 0.09 | Rb 0.05 | 0.67 | 1.35 |
| Comp. Ex. 1 | 12 | 0.83 | Ce 1.67 | | | 1.5 | 5.7 — | | | K 0.09 | Rb 0.05 | 0.67 | 2.50 |
| Comp. Ex. 2 | 12 | 1.35 | 0 | | | 2.0 | 7.7 — | | | K 0.09 | Rb 0.05 | 0 | 1.35 |
| Comp. Ex. 3 | 12 | 0.68 | Ce 0.68 | | | 1.9 | 7.3 — | | | K 0.09 | Rb 0.05 | 0.50 | 1.36 |
| Comp. Ex. 4 | 12 | 0.14 | Ce 1.21 | | | 1.7 | 6.7 — | | | K 0.09 | Rb 0.05 | 0.90 | 1.35 |
| Comp. Ex. 5 | 12 | 0.68 | Ce 0.68 | | | 1.9 | 3.5 Ni 2.0 | Mg | 2.0 | K 0.09 | Rb 0.05 | 0.50 | 1.36 |

| | Temperature (°C.) for firing of catalyst composition | Contact time (sec · g/cc) | Results obtained 100 hrs after the start of reaction | | Results obtained 700 hrs after the start of reaction | | Results obtained 1400 hrs after the start of reaction | |
|---|---|---|---|---|---|---|---|---|
| | | | Conversion (%) | Yield (%) | Conversion (%) | Yield (%) | Conversion (%) | Yield (%) |
| Example 1 | 580 | 6.5 | 99.6 | 80.7 | 99.4 | 80.2 | 99.2 | 79.8 |
| Example 2 | 570 | 6.5 | 99.6 | 81.9 | 99.4 | 81.6 | 99.3 | 81.4 |
| Example 3 | 580 | 6.5 | 99.5 | 82.0 | 99.4 | 81.7 | 99.3 | 81.4 |
| Example 4 | 570 | 6.5 | 99.7 | 81.3 | 99.5 | 81.0 | 99.3 | 80.7 |
| Example 5 | 580 | 6.5 | 99.6 | 81.2 | 99.4 | 80.8 | 99.2 | 80.4 |
| Example 6 | 570 | 6.5 | 99.5 | 81.0 | 99.3 | 80.6 | 99.0 | 80.1 |
| Example 7 | 590 | 6.5 | 99.5 | 82.0 | 99.3 | 81.7 | 99.2 | 81.5 |
| Example 8 | 610 | 6.5 | 99.7 | 81.8 | 99.5 | 81.5 | 99.3 | 81.2 |
| Example 9 | 600 | 6.5 | 99.6 | 81.9 | 99.4 | 81.6 | 99.3 | 81.4 |
| Example 10 | 590 | 6.5 | 99.6 | 82.0 | 99.4 | 81.7 | 99.2 | 81.4 |
| Example 11 | 590 | 6.5 | 99.6 | 80.6 | 99.4 | 80.3 | 99.2 | 80.0 |
| Example 12 | 600 | 6.5 | 99.6 | 80.5 | 99.5 | 80.3 | 99.3 | 80.0 |
| Example 13 | 600 | 6.5 | 99.7 | 81.4 | 99.5 | 81.2 | 99.3 | 81.0 |
| Example 14 | 620 | 6.5 | 99.6 | 80.9 | 99.3 | 80.7 | 99.1 | 80.5 |
| Example 15 | 580 | 6.5 | 99.5 | 81.8 | 99.3 | 81.5 | 99.1 | 81.2 |
| Comp. Ex. 1 | 580 | 6.5 | 99.6 | 79.6 | 99.4 | 78.6 | — | — |
| Comp. Ex. 2 | 570 | 6.5 | 99.4 | 82.5 | 99.1 | 80.8 | 98.7 | 77.9 |
| Comp. Ex. 3 | 580 | 6.5 | 99.5 | 81.9 | 99.3 | 80.6 | 99.1 | 79.2 |
| Comp. Ex. 4 | 590 | 6.5 | 99.6 | 76.2 | 99.1 | 75.4 | — | — |
| Comp. Ex. 5 | 590 | 6.5 | 99.5 | 81.5 | 99.2 | 80.0 | 98.9 | 78.5 |

Note: "—" means that data were not available because the operation of the production process was discontinued 700 hours after the start of reaction.

EXAMPLE 16

An ammoxidation catalyst composition, composed of oxides supported on 50% by weight, based on the total weight of the oxides and silica, of silica, having a structure represented by the formula:

was prepared in substantially the same manner as in Example 1. Using 1,000 g of an obtained catalyst composition supported on silica, an ammoxidation reaction of tert-butanol was conducted at 440° C. The contact time was 4.5 sec·g/cc. Results of the reaction were evaluated at time points of 100 hours, 700 hours and 1,400 hours after the start of reaction. As a result, it was found that 100 hours after the start of reaction, the conversion of tert-butanol was 99.6% and the yield of methacrylonitrile was 72.1%; that 700 hours after the start of reaction, the conversion of tert-butanol was 99.4%, and the yield of methacrylonitrile was 71.8%; and that 1,400 hours after the start of reaction, the conversion of tert-butanol was 99.1%, and the yield of methacrylonitrile was 71.5%.

INDUSTRIAL APPLICABILITY

By use of the ammoxidation catalyst composition of the present invention in producing acrylonitrile from propylene, or methacrylonitrile from isobutene or tert-butanol, by ammoxidation of the propylene or of the isobutene or tert-butanol, not only can acrylonitrile or methacrylonitrile be produced in high yield, but also the ammoxidation reaction can be stably conducted even when the operation of the production process is conducted for a prolonged period of time, so that a lowering of the yield of acrylonitrile or methacrylonitrile, relative to the yield thereof at the initial stage of reaction, is very small.

We claim:

1. An ammoxidation catalyst composition for use in producing acrylonitrile from propylene, or methacrylonitrile from isobutene or tert-butanol, by ammoxidation of said propylene or of said isobutene or tert-butanol, comprising an oxide catalyst composition represented by the formula (I):

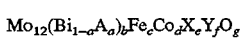 (I)

wherein:

A is at least one rare earth element,

X is at least one element selected from the group consisting of nickel, magnesium, zinc and manganese, Y is at least one element selected from the group consisting of potassium, rubidium and cesium, a is the atomic ratio of A to the sum of bismuth and A, b is the atomic ratio of the sum of bismuth and A, relative to twelve atoms of molybdenum, and c, d, e, f and g are, respectively, the atomic ratios of iron, cobalt, X, Y and oxygen, relative to twelve atoms of molybdenum, wherein
   a is a number of from 0.6 to 0.8,
   b is a number of from 0.5 to 2,
   c is a number of from 0.1 to 3,
   d is a number of from more than 0 to 10,
   e is a number of from 0 to 8,
   f is a number of from 0.01 to 2, and
   g is a number determined by the valence requirements of the other elements present.

2. The catalyst composition according to claim 1, wherein A in formula (I) is at least one element selected from the group consisting of yttrium, lanthanum, cerium, praseodymium, neodymium and samarium.

3. The catalyst composition according to claim 1, wherein A in formula (I) is cerium.

4. The catalyst composition according to claim 1, wherein b, c, d, e and f in formula (I) are, respectively, from 0.7 to 1.8, from 0.5 to 2.5, from 0.5 to 8, from 0 to 8, and from 0.02 to 1, relative to twelve atoms of molybdenum.

5. The catalyst composition according to claim 1, wherein e in formula (I) is from 0.1 to 6, relative to twelve atoms of molybdenum.

6. The catalyst composition according to any one of claims 1 to 5, which further comprises silica as a carrier having said oxide catalyst composition supported thereon, wherein said silica carrier is present in an amount of from 30 to 70% by weight, based on the total weight of said oxide catalyst composition and said silica carrier.

7. A process for producing acrylonitrile from propylene, or methacrylonitrile from isobutene or tert-butanol, by ammoxidation of said propylene or of said isobutene or tert-butanol, which comprises reacting propylene with, or reacting isobutene or tert-butanol with molecular oxygen and ammonia at a temperature of from 350° C. to 550° C. under a pressure of from atmospheric pressure to 3 atm in the presence of an ammoxidation catalyst composition comprising an oxide catalyst composition represented by the formula (I):

$$Mo_{12}(Bi_{1-a}A_a)_b Fe_c Co_d X_e Y_f O_g \qquad (I)$$

wherein:

A is at least one rare earth element,

X is at least one element selected from the group consisting of nickel, magnesium, zinc and manganese, Y is at least one element selected from the group consisting of potassium, rubidium and cesium, a is the atomic ratio of A to the sum of bismuth and A, b is the atomic ratio of the sum of bismuth and A, relative to twelve atoms of molybdenum, and c, d, e, f and g are, respectively, the atomic ratios of iron, cobalt, X, Y and oxygen, relative to twelve atoms of molybdenum, wherein
   a is a number of from 0.6 to 0.8,
   b is a number of from 0.5 to 2,
   c is a number of from 0.1 to 3,
   d is a number of from more than 0 to 10,
   e is a number of from 0 to 8,
   f is a number of from 0.01 to 2, and
   g is determined by the valence requirements of the other elements present.

8. The catalyst composition according to claim 7, wherein A in formula (I) is at least one element from the group consisting of yttrium, lanthanum, cerium, praseodymium, neodymium and samarium.

9. The catalyst composition according to claim 7, wherein A in formula (I) is cerium.

10. The process according to claim 7, wherein b, c, d, e and f in formula (I) are, respectively, from 0.7 to 1.8, from 0.5 to 2.5, from 0.5 to 8, from 0 to 8 and from 0.02 to 1, relative to twelve atoms of molybdenum.

11. The process according to claim 7, wherein e in formula (I) is from 0.1 to 6, relative to twelve atoms of molybdenum.

12. The process according to any one of claims 7 to 11, which further comprises silica as a carrier having said oxide catalyst composition supported thereon, wherein said silica carrier is present in an amount of from 30 to 70% by weight, based on the total weight of said oxide catalyst composition and said silica carrier.

13. The process according to any one of claims 7 to 11, wherein said molecular oxygen is in the form of air.

14. The process according to any one of claims 7 to 11, wherein the molar ratios of propylene, or isobutene or tert-butanol:ammonia:oxygen are in the range of 1:0.8 to 1.4:1.4 to 2.4.

15. The process according to any one of claims 7 to 11, wherein said reaction is conducted in a fluidized bed reactor.

* * * * *